United States Patent [19]

Huiskes et al.

[11] Patent Number: 5,314,494
[45] Date of Patent: May 24, 1994

[54] ENDO-PROSTHESIS, A FEMORAL HEAD PROSTHESIS AND AN ACETABULUM PROSTHESIS

[75] Inventors: Hendrik W. J. Huiskes, Wijchen; Franciscus A. M. Ypma, Oudkerk; Pierre J. T. M. Jaspers, Utrecht, all of Netherlands

[73] Assignee: Orthopaedic Technology B.V., Bilthoven, Netherlands

[21] Appl. No.: 40,571

[22] Filed: Mar. 31, 1993

Related U.S. Application Data

[60] Continuation of Ser. No. 642,656, Jan. 17, 1991, abandoned, which is a division of Ser. No. 267,095, Nov. 3, 1988, Pat. No. 5,041,141.

Foreign Application Priority Data

Nov. 3, 1987 [NL] Netherlands .................. 87 02626

[51] Int. Cl.$^5$ .............................................. A61F 2/32
[52] U.S. Cl. ........................................ 623/23; 623/18
[58] Field of Search ..................... 623/16, 18, 19, 20, 623/22, 23

[56] References Cited

U.S. PATENT DOCUMENTS

| Re. 28,895 | 7/1976 | Noiles ................. | 623/22 |
| 3,818,512 | 6/1974 | Shersher ............... | 623/22 |
| 3,820,167 | 6/1974 | Sivash ................. | 623/22 |
| 3,843,975 | 10/1974 | Tronzo ................. | 623/23 |
| 3,894,977 | 7/1975 | Mittelmeier et al. ..... | 623/22 |
| 4,031,571 | 6/1977 | Heinke et al. .......... | 623/23 |
| 4,068,324 | 1/1978 | Townley et al. ......... | 623/23 |
| 4,851,004 | 7/1989 | Homsy ................. | 623/16 |
| 4,919,665 | 4/1990 | Homsy ................. | 623/23 |
| 5,061,287 | 10/1991 | Feller ................. | 623/23 |

FOREIGN PATENT DOCUMENTS 3132543 6/1982 Fed. Rep. of Germany ........ 623/23

*Primary Examiner*—David Isabella
*Attorney, Agent, or Firm*—Watson, Cole, Grindle & Watson

[57] ABSTRACT

A prosthesis for insertion into a long bone includes a stem which has been shaped so as to evenly distribute low stress to the bone. A synthetic resinous sheath surrounds the stem which effects a contact surface between the stem and the bone. The prosthesis includes an extension which extends outwardly of the bone and has a ball and socket thereon.

11 Claims, 4 Drawing Sheets

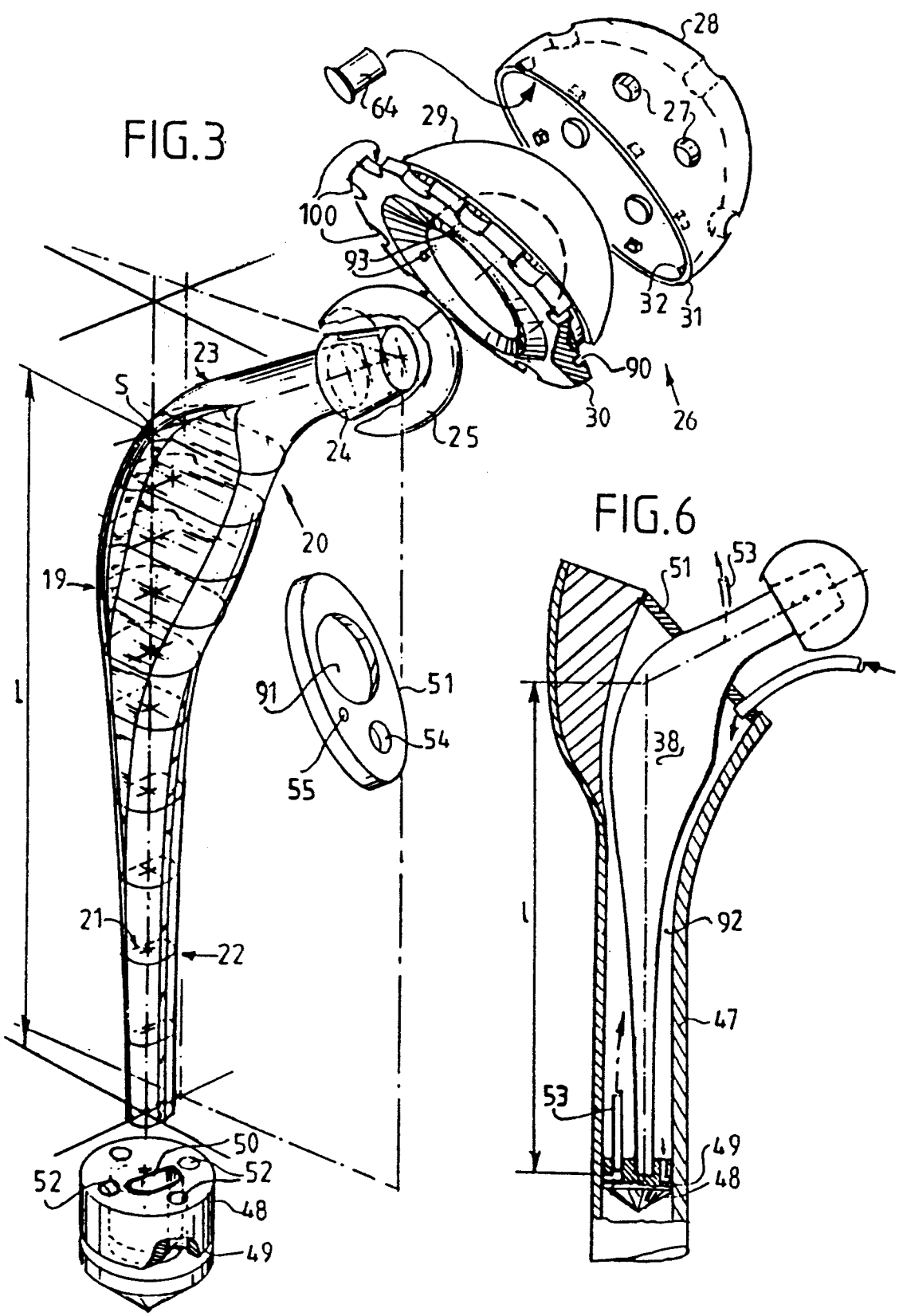

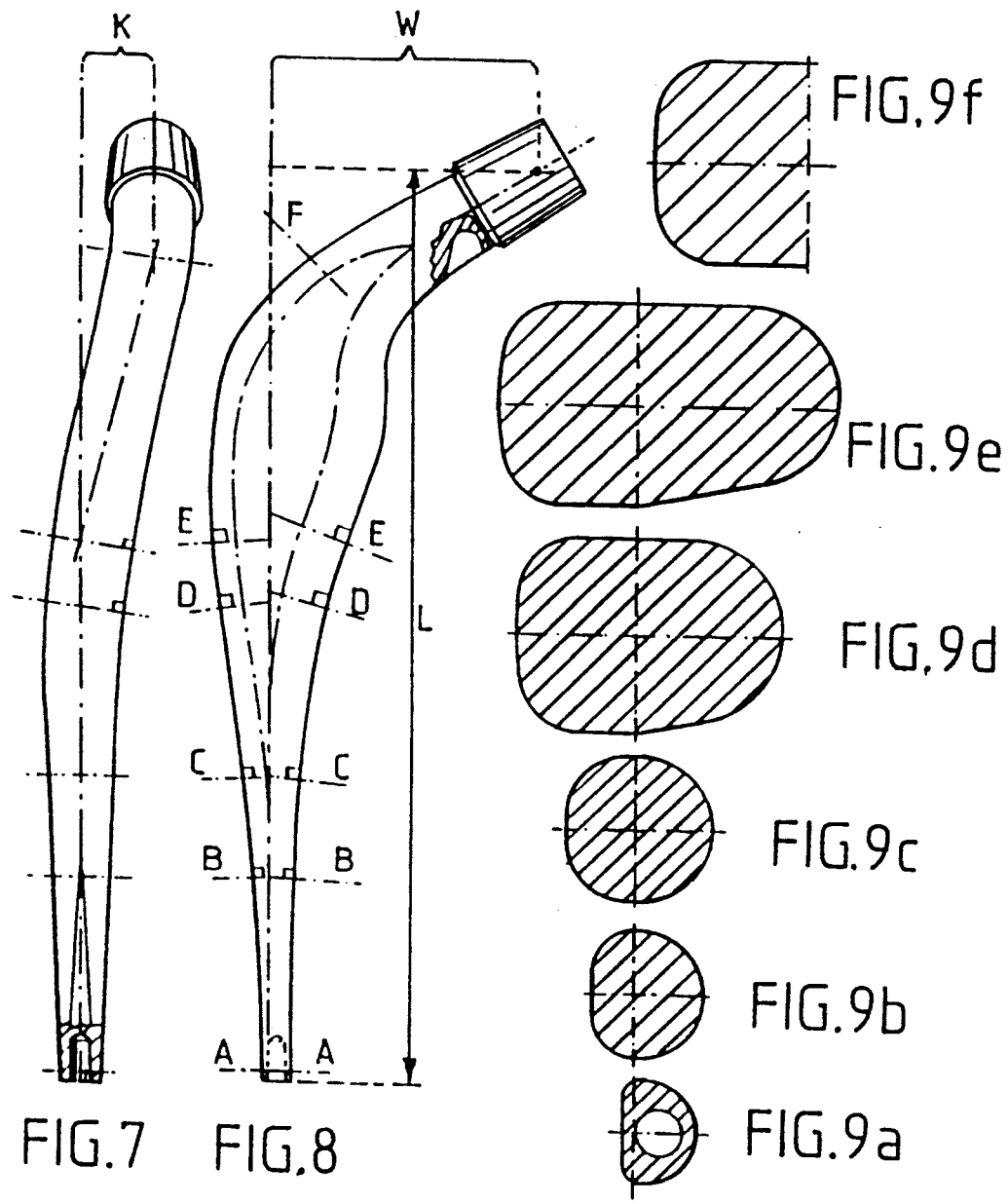

ENDO-PROSTHESIS, A FEMORAL HEAD PROSTHESIS AND AN ACETABULUM PROSTHESIS

CROSS REFERENCE TO RELATED APPLICATION

This application is a continuation of application Ser. No. 07/642,656, filed Jan. 17, 1991, now abandoned, which is a divisional of application Ser. No. 07/267,095 filed Nov. 3, 1988, now U.S. Pat. No. 5,041,141.

BACKGROUND OF THE INVENTION

A first aspect of the present invention relates to designing prostheses in general and more particularly femoral head prostheses and acetabulum prostheses.

Prior art in this field comprise:

Article from Biomedizinische Technik, Vol. 30, Nr. 5, G. Giebel et al.: "Fertigung von Knochenmodellen nach Computer-Tomographie-Daten zur Verwendung in Chirurgie und Orthopädie" (pages 111–114);

Lecture during First European Congress of Knee Surgery and Arthroscopy, Apr. 9–14 1984, Berlin, issued by E. L. Trickey et al. Springer-verlag, Berlin, Heidelberg, DE U. Munzinger et al.: "Biomechanics of Knee Prostheses" (pages 324–334);

U.S. Pat. No. 4,153,953 (Grobbelaar), column 3, pages 19–28, 56–61;

DE-A-2805868 (Engelbrecht et al.), FIG. 1;
GB-A-2096003 (Burstein), page 2;
EP-A-0149527 (Lee et al.), FIGS. 1, 2
GB-A-2045082 (Raab), page 1

It is a first object of the method according to the present invention to improve upon the prior art.

It is a further object to provide a method in which tensile, compressive and shear stresses acting on the interface between prosthesis and bone, whether or not provided with a cement mantel, are controllable. Theories exist that resorption or necrosis of bone are caused by stress shielding of the bone due to the prosthesis.

A preferred method according to the present invention concerns prostheses minimizing local normal and shear stresses between bone and prosthesis. Existing endoprostheses used in practice generally consist of a metal core surrounded by a mantle of an artificial material which is in direct contact with the bone. According to the present invention, a mathematical simulation model is made of such a construction, by means of the so-called finite element method. With this model the stresses which act on the connecting planes or at an interface area between the artificial mantle and the bone can be calculated. These stresses depend, amongst others, on the geometry of the prosthesis. By means of a mathematical search procedure that geometry can be determined which creates a prechosen stress pattern at the interface between bone and prosthesis.

The above-mentioned method was applied to a 2-D model of a femoral head prosthesis and a acetabular prosthesis.

A second aspect of the present invention relates to a femoral head prosthesis having a specific shape.

The characteristics of this shape are not known from the prior art, e.g.:

DE-A-3.243.861; DE-A-2.805.868; BE-A-2.247.721; GB-A-2.078.523; GB-A+2.045.082; EP-A-146.192; EP-A-12.146; and U.S. Pat. No. 4,021,865.

A third aspect of the present invention is directed to a method for the positioning of an endo-prosthesis in a bone as well as spacing or positioning elements.

From the prior art a more cumbersome method for introducing a femoral head prosthesis is known from U.S. Pat. No. 4,718,909.

According to the fourth aspect of the present invention an acetabular prosthesis having a characteristic shape is provided. Those characteristic shapes are not known from the prior art, viz. U.S. Pat. Nos. 4,566,138 and 4,563,778.

Malfunctioning of a human joint due to arthrosis, arthritis, trauma conditions or any other cause reduces the well-being of the person concerned and is expensive for society at large. With increasing success, such defects are corrected by joint arthroplasty. Annually in the world, these procedures are carried out more than 500,000 times. Most defects concern the hip and the knee joints; however, ankles, toes, shoulders, elbows, wrists and finger joints can also be provided with artificial joints.

The known prostheses usually consist of a combination of a metal and a plastic. Most prostheses have a metal stem or plateau which is fixed within the bone by means of acrylic cement. Acrylic cement is a fast curing mixture of monomethyl-methacrylate liquid and polymethylmethacrylate powder. This viscous mass can be introduced into the intramedullary canal or into the trabecular bone of a bone. Subsequently, the prosthesis is inserted in the acrylic cement mass. After curing, a mantle of cement remains in between the metal core and the bone. The bone cement does not have any adhesive properties, and the connection between the cement and the bone is merely realized by mechanical interlock. A firm interlock is achieved by a sufficiently deep penetration of the cement into the trabecular bone. This penetration arises if the acrylic cement has a sufficiently low viscosity and is pressurized for some time.

In cases where no acrylic cement is used, the prosthesis is introduced directly into the bone. Such a prosthesis can be made out of metal completely, or can be composed out of a metal core and a coating. In this case there is not primary fixation between the prosthesis and the bone. Such a fixation can, however, be accomplished by the ingrowth of bone into the surface structures of the prosthesis.

A well-known long-term complication of surgical joint replacement is loosening of the prosthesis. This loosening mostly occurs at the interface between prosthesis and bone. It is known that the chances for this complication to occur increase with decreasing age of the patient at the time of the operation and an accordingly increased activity level. Loosening of the prosthesis leads to resorption of bone and finally to severe complaints of pain. These complaints can be so dramatic that a revision operation is indicated, in which the old prosthesis is removed and a new one is inserted. However, the long-term results of a revision operation are not as good as those of a primary joint replacement, and the revision procedure cannot be repeated an arbitrary number of times.

No common opinion exists presently on the cause or etiology of loosening. The following possibilities have been suggested: necrosis of the bone at the interface caused by toxicity of the cement monomer or excessive heat release due to the exothermally curing bone cement, fracture of the cement mantle due to mechanical loading, failure of the interface caused by local stress peaks, reduced loading of the bone caused by stress shielding, etc.

Further advantages, features and details of the invention will be clarified by reference to the accompanying drawings.

BRIEF DESCRIPTION OF THE DRAWINGS

FIG. 3 is a perspective, partly exploded view with cross-sections on several levels of a preferred design of a femoral head prosthesis in accordance with the present invention.

FIG. 6 is a schematic view illustrating the procedure for the fixation of a femoral head prosthesis.

FIGS. 7, 8 and 9A–9F are views of a second embodiment of a femoral head prosthesis according to the present invention, showing a back view, side view and section views respectively.

Figure 5A:
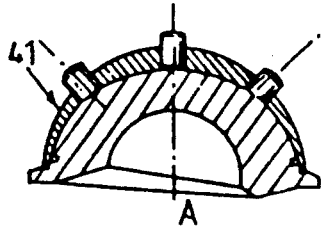
FIGS. 5A–5G depict seven acetabular prostheses shaped in accordance with the present invention.
Figure 5B:
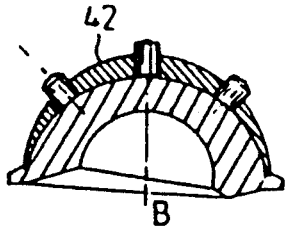
Figure 5C:
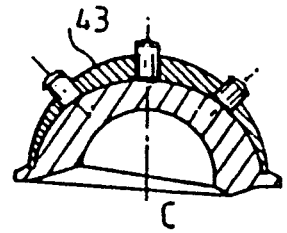
Figure 5D:
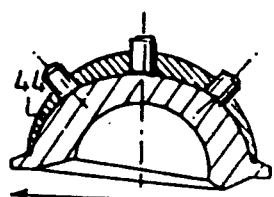
Figure 5E:
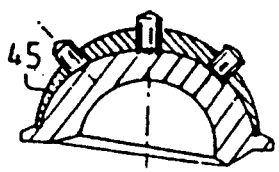
Figure 5F:
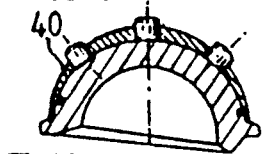
Figure 5G:
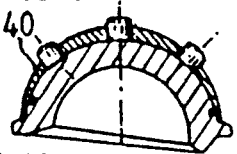

DETAILED DESCRIPTION OF THE PREFERRED EMBODIMENTS:

Loosening of a prosthesis can be caused by mechanical overloading of the interface between acrylic cement and bone. Particularly meant here is the occurrence of peaks in the normal and shear stresses at the interface, and the occurrence of high strain energy density levels in the cement at the interface. According to the present invention, the stress patterns at the interface between bone and cement of an existing prosthesis were calculated by means of a finite element model. In such a model a particular geometry is approximated with a finite number of elements. For this model the external load, the material properties and the boundary conditions are provided as well. By means of advanced digital computers stresses and strains in the model can be calculated.

The desired stress patterns are taken as the objective for a mathematical search or optimization procedure to determine that geometry which generates those stress patterns which approximate the desired ones best.

In a finite element model (FIG. 1) the elements 10, 11 and 12 represent cortical bone, the elements 3, 4 represent trabecular bone, the elements 5, 9 (9') represent bone cement, and the elements 6, 7 and 8 represent the prosthesis.

An arbitrarily chosen initial prosthesis geometry G (FIG. 2)—for example the geometry of a known prosthesis—is introduced in a bone model at 13. At 14 the external load M, the material properties E, and the boundary conditions B are provided. At each nodal point -i- of the prosthesis-bone interface the stresses are calculated and substituted in a function $f_i = f$ (normal stress:, shear stress$_i$, tangential stress$_j$). A weight-factor $w_i$ is assigned to the function $f_i$ in each node,-i- and all functions are added in the objective function $F_G =$ $$F_G = \sum_{i=1}^{n} w_i \cdot f_i,$$

related to the initial geometry G.

The objective function $F_G$ in 15 depends on the design criterion D, representing the desired stress patterns. The function $F_G$ is minimized; for example in the function $f_i$ the stresses are raised to a higher even power, for example 6, so that peaks in the stress values can be smoothened. For example $f_i = U_i^3$ with U the strain energy at nodal point -i-.

Next a nodal point -j- of the interface between the metal stem and the cement mantle is moved over a small distance, so a new geometry $G_j$ is created. Of this new geometry the function $f_{Gj}$ is calculated. This is done for all nodal points -j-. The functions $F_{Gj}$ obtained are compared with $F_G$. Depending on the decrease of the function $F_{Gj}$ compared to the starting function $F_G$, the geometry G is converted to G' by means of an algorithm 16—a so-called least-P algorithm—so that $F_{G'}$ is smaller than $F_G$. Subsequently, the geometry G' is substituted via feed-back loop 17 and the procedure is restarted. When the desired geometry defined by criterium D is attained, the function $F_{G'}$ will not decrease anymore and the procedure is terminated at 18.

Hereafter the shapes of the prostheses obtained with the above-mentioned designed method will be shown, in particular a femoral head prosthesis and an acetabular prosthesis; it may be evident that the above-mentioned method is also applicable to other prostheses.

Figure 1:
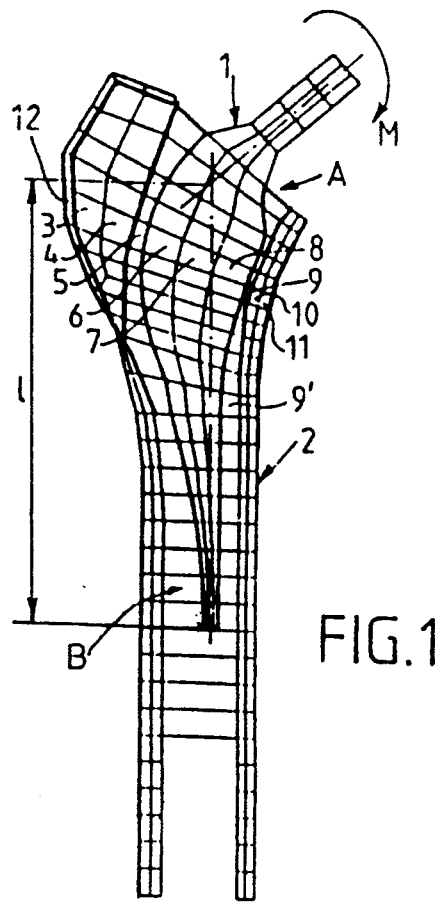
FIG. 1 is a schematic frontal view of a preferred design of
a femoral head prosthesis in accordance with the present invention.

In the model shown in FIG. 1 the real three-dimensional structure was approximated by a side-plate behind the element mesh or grid shown in FIG. 1, which connects the medial and lateral cortical bone. This sideplate has the material properties of cortical bone.

Figure 2:
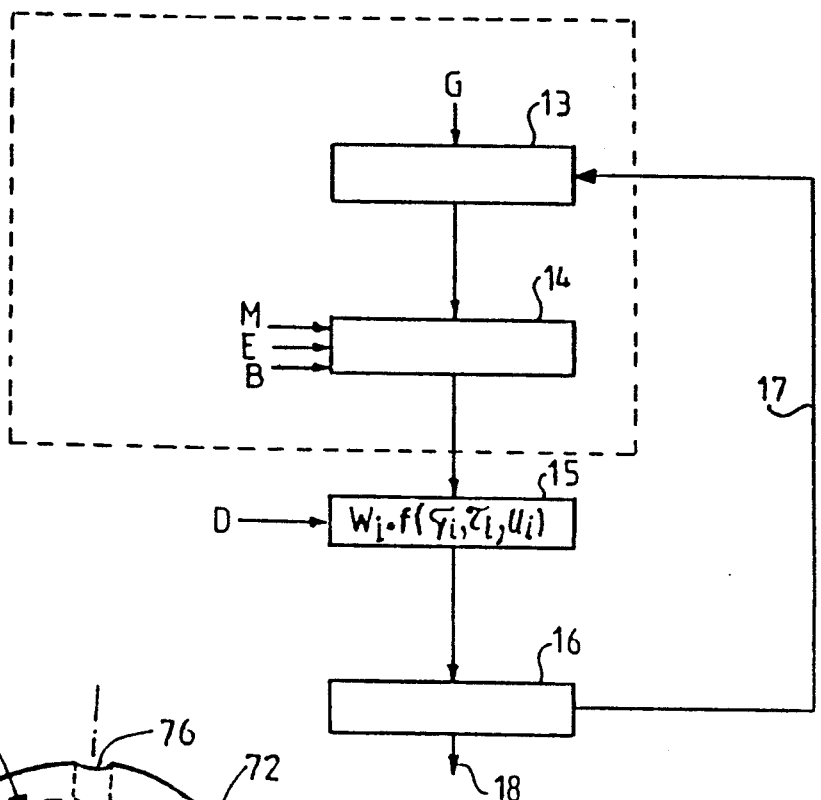
FIG. 2 is a preferred design of the algorithm for the shaping of the prosthesis of FIG. 1.

The design criterion for the prosthesis 1 in FIG. 1 for the application of the procedure of FIG. 2 is as follows:

Shear and normal stresses as low as possible.

A uniform distribution of the shear stresses.

A uniform distribution of the normal stresses.

No tensile stresses between cement and cortical bone.

Limited tensile stresses between cement and trabecular bone.

Low strain energy density in the cement near the interface.

The geometry (FIGS. 1 and 3) thus found hardly shows sensitivity for the nature of the external load (moment or force) on the head 25 of the prosthesis. However, the material of the prosthesis 1, 20 (stainless steel, CoCrMo, titanium) does significantly change the design. The present examples are based on the selection of CoCrMo as prosthetic material.

The distinct features of the design shown in FIG. 3 can be described as follows:

a metal stem 22 with a proximal taper;

the stem has a distal taper;

after insertion of the stem into the bone the stem tip must be located medially of the intramedullary axis;

the cement mantel (FIG. 1) has at the medial side at the resection plane a thickness of ±10 mm;

the cement mantle at the medial side, from 1½ cm beneath the resection plane towards distally, displays a slowly increasing thickness from 2 to 4½ mm; from halfway down unto the stem tip at the cement mantle on the medial side remains 4½ mm thick;

the thickness of the cement mantle at the lateral distal side increases downwards unto the stem tip.

The prostheses 20 (FIG. 3) consists of a stem 22, a neck 23, and a cone 24, on which a femoral head 25 can be positioned. This modular system gives the possibility of choosing a variable neck length and a variable material for the femoral head (possibly including ceramic or other artificial material). From FIG. 3 it can be seen further that the distal lateral side of the prosthesis 21 is plane, while ending upwards in a widened and rounded back 19, which contains flanges or ribs on the anterior and posterior sides. These flanges or ribs produce a stiffening of the proximal stem and cause a favorable stress distribution in the cement mantle. A characteristic length between the distal stem tip and the intersection of the neck axis and the intramedullary axis amounts to 125 mm. As the drawings are made to scale, other characteristic dimensions can be read from FIG. 3.

Figure 4:
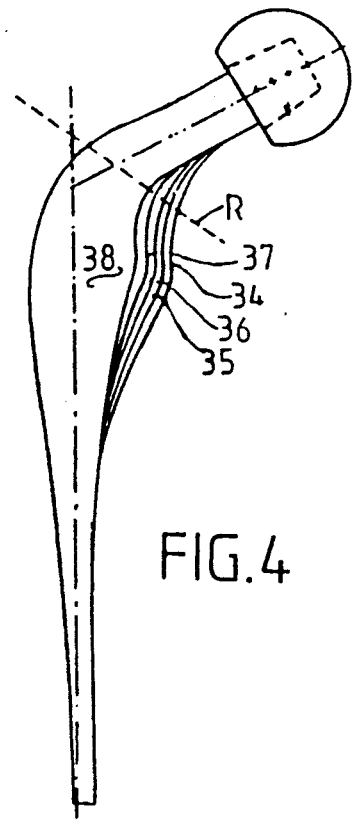
FIG. 4 depicts five femoral head prostheses shaped in accordance with the present invention.

With a total of 5 metal protheses 34-38 (FIG. 4) a patient population can be provided with a well fitting prosthesis in almost all cases; the prostheses 34-38 differ in their dimensions at the medial proximal side only. With one of the prostheses 34-38 a series of bones can be served, in order to approximately create the stress patterns aforementioned.

An acetabular prosthesis 26 (FIG. 3) designed in accordance with the present invention consists of an insert 29 out of UHMWPE (Ultra High Molecular Weight Polyethylene) and a metal backing 28. The geometry which is shaped in accordance with the same criteria as described for the femoral head prosthesis can be seen in FIGS. 3 and 5 and can be described as follows;

a rim 30 to ensure a constant cement thickness of 3 mm;

a metal backing of nonuniform thickness;

a metal backing which continues at the lateral superior side unto the acetabular outer plane;

a metal backing which continues at the medial inferior side unto the acetabular plane as far as possible;

a metal backing which is nowhere thicker than 1 mm at the periphery; and a metal backing which has its maximal thickness of for example 5 mm at its center or in its near surrounding.

The outside diameter of the metal backing (FIGS. 5A-5G) is in between 46 and 58 mm including the cement mantle. A femoral head diameter of 28 mm and a minimal polyethylene thickness of 5 mm has been chosen. All other dimensions are listed in Table 1.

TABLE 1

| \ | Acetabular cup dimensions in mm for 7 sizes. | | | | |
|---|---|---|---|---|---|
| outside diameter | cement-mantle thickness | periferal backing thickness | central backing thickness | central polyethylene thickness | position headcenter outside acetabular plane |
| 46 | 3 | 1 | 1½ | 5¼ | ¼ |
| 48 | 3 | 1 | 2 | 5½ | ⅛ |
| 50 | 3 | 1 | 2½ | 5¾ | ⅛ |
| 52 | 3 | 1 | 3 | 6 | 0 |
| 54 | 3 | 1 | 4 | 6 | 0 |
| 56 | 3 | 1 | 5 | 6 | 0 |
| 58 | 3 | 1 | 5 | 7 | 0 |

The cup is also provided with spacers 64, which are mounted in holes 27 in the metal backing 28, to ensure uniform thickness of the cement mantle at insertion. The polyethylene insert 29 is mounted into the metal backing 28 by means of recessions and studs 32. The insert is provided with a rim 30 which is provided with a groove 90 to contain a rim 31 of the metal backing 28. The rim 30 serves to position the acetabular prosthesis in the reamed pelvis and to enable pressurization of cement during the operation, as will be described hereafter. The mound of the polyethylene insert is positioned at an angle of 10 degrees to the acetabular plane, to prevent luxation of the femoral head 25.

When the geometry of a femoral head prosthesis has been shaped accurately as described above, also considering the shape of the cement mantle, such a prosthesis 38 (FIG. 6) has to be positioned accurately. However, also a prosthesis not designed according the method mentioned above can be positioned with the method described hereafter. After resection of the femur at plane R (FIG. 4) the intramedullary canal of the femur is reamed cylindrically. By means of a rasp with a smooth distal stem serving as a guide in the drill hole, the proximal femur is rasped to size accurately. With the rasp itself in situ as a mould, an accurate recession is made to contain a proximal spacer 51.

The prosthesis 38, provided with two spacers 51 and 48 (FIGS. 3, 6) is positioned into the bone 47. The first spacer 51 is positioned at the level of the resection plane on the proximal stem. Apart from an opening 91 for the prosthesis, the proximal spacer 51 contains a hole 55 for the airvent tube 53, and a hole 54 for the injection of bone cement. The proximal spacer 51 in this way positions the proximal stem and blocks the femoral canal 92, which must be cemented.

The second spacer 48 fits in the cylindrically drilled diaphysis 34 with minimal play, ensures an accurate positioning of the stem tip with respect to the bone 47, and also seals the lower side of the femoral canal 37. The distal spacer 48 is provided with a number of canals 52 over its length, which are interconnected by a circular groove 49.

During cementing, an airvent tube 53 is installed with one end in one of the canals 52. After bushing and rinsing of the intramedullary space, the assembly of the prosthesis 38, spacers 58 and 51, and airvent tube 53 is inserted. The remaining intramedullary space is thus cemented secondarily. Through the filler opening 54, cement is injected in the femoral canal 37; for example by means of a cement gun (not shown here) with small nozzle diameter. After filling of the canal the cement can be pressurized in order to penetrate into the canals 52 of the distal spacer and into the bone 47. Cement injection can also take place through a hole to be drilled through a part of the bone structure.

The spacers 48 and 51 are preferably made of PMMA (polymethylmethacrylate) in order to form a firm bond with the cured cement. After pressurizing the bone cement for a short period of time, the airvent tube 53 can be retrieved slowly, while the cement mass is kept pressurized. The space remaining after removal of the airvent tube 53 will be filled with cement.

The airvent tube 53 serves for the drainage of air, fluids and bone marrow which is pushed down the femoral canal 37 by the cement during cementing. In order to achieve a firm interlock between the cement and the bone, the cement can also be kept pressurized after the removal of the airvent tube 53.

Although the method described here refers to a femoral head prosthesis, it can also be applied for the positioning and fixation of all other prostheses, provided with a stem to be positioned in a long bone. The opening 50 in the distal spacer 51 is not circular and is located eccentrically; when applied to another prosthesis this opening 50 can for example be circular or be located centrally.

The second embodiment of a femoral head prosthesis according to the present invention (FIGS. 7, 8 and 9) can by means of the bent shape determined by the dimension K relative to L and W, more easily be removed from a bone, which is important for revision operations.

Further the shown shape lacks the flanges or ribs from the first embodiment, providing more space for the applying of a cement mantle.

Preferably K has a value of 11.25 mm relative to a dimension L of 135 mm and a dimension W of 41 mm, relating to a mid-size prosthesis.

Figure 10:
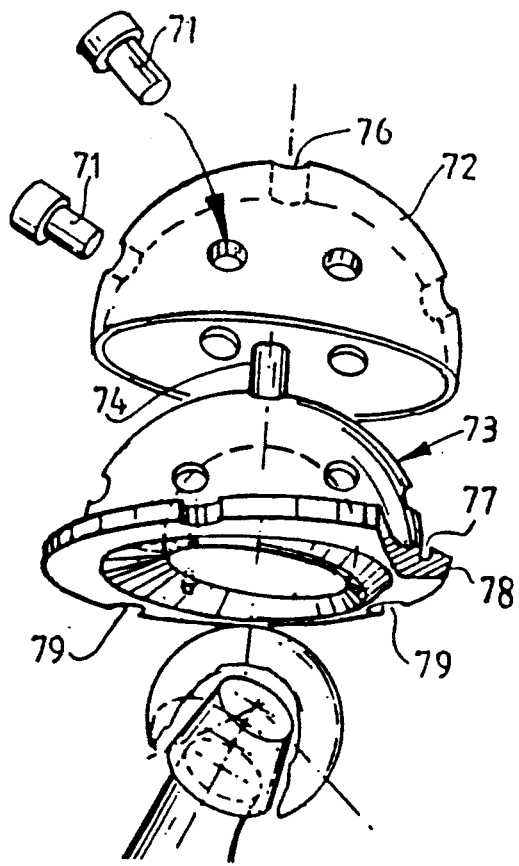
FIG. 10 is an exploded view of a second embodiment of an acetabular prosthesis according to the present invention.

A second embodiment of the acetabular prosthesis according to the present invention (FIG. 10) shows spacers 71, preferably of polyethylene, to be inserted from the outside into backing 72. Insert 73 is provided with a fixed central element 74 to be inserted in central hole 76. The insert 73 is provided with a groove 77 disposed in a rim 78 provided with three notches 79 equally spaced around the periphery of insert 73.

What is claimed is:

1. A femoral head prosthesis for insertion into a long bone having a canal therein disposed along an intramedullary axis of the long bone which has been resected along a resection plane to expose the interior canal thereof, and wherein said prosthesis is modeled relative to the long bone, said prosthesis comprising a neck extending above the resection plane wherein the prosthesis is inserted into the long bone; and an elongated stem having a continuous protrusion formed with a proximal taper and a distal taper said proximal taper extending continuously only along the medial side to an area below the resection plane terminating in a apex region of said protrusion and the digital taper extending continuously from the apex region of said protrusion distally and continuously only along the medial side, such that, after having been inserted into the canal, the resulting stresses between said stem and contact surfaces between the stem and the long bone defining the canal are minimized and evenly distributed in accordance with said model.

2. A femoral head prosthesis according to claim 1 of which the distal taper is slimmer than the proximal taper.

3. A femoral head prosthesis according to claim 1, wherein the stem includes a distal tip portion located for positionment medially of an intramedullary axis of the long bone.

4. A femoral head prosthesis according to claim 1 further including a positioning element sized for fitting over the neck of the femoral head prosthesis, said positioning element to be positioned along the resection plane.

5. A femoral head prosthesis according to claim 4 wherein said positioning element has a first hole in communication with the canal for receiving an air venting tube.

6. The femoral head prosthesis according to claim 4 wherein said positioning element has a second hole in communication with the canal for injection of an acrylic cement therein.

7. A prosthesis as defined in claim 1 wherein said prosthesis include a ball attached to the neck.

8. A prosthesis as defined in claim 1 including a synthetic resinous sheath surrounding said stem, which sheath effects a contact surface between the stem and the bone canal.

9. A femoral head prosthesis according to claim 3 further including a positioning element to be positioned at a distal location within the long bone, said positioning element having an off center hole for receiving the distal stem tip therein medially of said intramedullary axis.

10. A femoral head prosthesis according to claim 9, wherein said positioning element has a chamber having an inlet and an outlet adapted for communication with the canal, said outlet adapted for receiving an air venting tube.

11. A femoral head prosthesis for insertion into a long bone having a canal therein disposed along an intramedullary axis of the long bone which has been resected along a resection plane to expose the canal interior thereof, said prosthesis comprising a stem and a having a narrow distal portion and terminal stem tip and a widened proximal portion below the resection plane and a neck portion extending between the widened proximal portion to the femoral head above the resection plane, a first spacer having an opening for receiving the neck therein and for abutting the long bone along the resection plane, said first spacer for radially positioning the neck with respect to the canal, and a second spacer having an opening disposed off center thereof for receiving the terminal stem tip therein medially of said intramedullary axis and for closely engaging a distal inner wall portion of the canal for positioning the narrow stem portion within said canal, said second spacer being formed with a through opening having an inlet and an outlet in communication with the interior of the long bone, and said distal and proximal portions having a shape, such that, after having been inserted into the canal, stresses between said stem and the bone defining the canal have values which are minimized and evenly distributed therealong.

* * * * *